United States Patent [19]

Dejaiffe

[11] Patent Number: 4,721,389
[45] Date of Patent: Jan. 26, 1988

[54] METHOD AND APPARATUS FOR MEASURING RETROREFLECTIVITY OF A REFLECTIVE LAYER ON A SURFACE

[75] Inventor: Robert Dejaiffe, Oak Ridge, N.J.

[73] Assignee: Potters Industries, Inc., Hasbrouck Heights, N.J.

[21] Appl. No.: 724,774

[22] Filed: Apr. 18, 1985

[51] Int. Cl.⁴ .............................................. G01N 21/55
[52] U.S. Cl. ..................................... 356/445; 356/447
[58] Field of Search .......................... 356/445, 447, 448

[56] References Cited

U.S. PATENT DOCUMENTS

| | | | |
|---|---|---|---|
| 2,334,578 | 11/1943 | Potters | 49/57 |
| 2,619,776 | 12/1952 | Potters | 49/58 |
| 2,947,115 | 8/1960 | Wood | 49/58 |
| 3,700,903 | 10/1972 | Adler et al. | 356/447 X |
| 3,782,827 | 1/1974 | Hisenson et al. | 356/120 |
| 3,866,032 | 2/1975 | Veres | 240/1.2 |
| 3,922,093 | 11/1975 | Dandliker et al. | 356/448 X |
| 3,994,586 | 11/1976 | Sharkins et al. | 356/445 X |
| 4,097,751 | 6/1978 | Egan et al. | 350/571 |
| 4,368,982 | 1/1983 | Van Arnam et al. | 356/445 |
| 4,505,590 | 3/1985 | Heenan | 356/445 |

FOREIGN PATENT DOCUMENTS 75422 3/1983 European Pat. Off. .
2067748 7/1981 United Kingdom .

*Primary Examiner*—Eugene R. LaRoche
*Assistant Examiner*—James C. Lee
*Attorney, Agent, or Firm*—Lee C. Robinson, Jr.

[57] ABSTRACT

A retroreflectivity measuring system measures performance data relating to a reflective surface, such as a highway stripe or marking containing reflective glass beads. A laser beam illuminates a portion of the reflective surface with radiation of a predetermined wavelength, the laser being incident on the surface at an incidence angle i. The incident laser beam is then reflected back, at least partially, at a particular observation angle o that is separated from the incidence angle by a divergence angle δ. A telephotomultiplier aimed at the illuminated area receives the reflected laser beam at the observation angle o. A preferred telephotomultiplier includes a telescope, a narrow pass optical filter for passing basically only the wavelength of the laser beam, and a sensitive photoelectric device, such as a multiplier phototube. The laser and the telephotomultiplier may be mounted on a servo-motor driven frame in order to scan the target area from a moving vehicle.

18 Claims, 11 Drawing Figures

METHOD AND APPARATUS FOR MEASURING RETROREFLECTIVITY OF A REFLECTIVE LAYER ON A SURFACE

BACKGROUND OF THE INVENTION

This invention relates to the measurement of retroreflectivity, especially such measurement of a retroreflective medium. The invention is more particularly directed to a technique for measuring retroreflectivity of a reflective medium in which a laser is used to illuminate an area of the medium with a known quantity of light at a selected incidence angle, which light is reflected back and measured at a selected observation angle.

The present invention, while of general application, finds particular utility in surveys of retroreflective traffic markings on highways or roadways, especially painted stripes in which retroreflective beads of glass or other material are located on the painted surface.

Thus far, no instrumentation has been developed for measuring the performance of highway stripes and detecting bead erosion on a continuous basis, which is convenient to use at troublesome spots, such as at curves, bridge approaches, etc. Previously, bead erosion at such places was discovered primarily if a motorist happened to report heavy wear at that area. Also, because of the nature of the retroreflective particles, their reflective properties could reasonably be tested only at night or under other conditions of substantial darkness.

SUMMARY OF THE INVENTION

It is an object of this invention to provide a method and apparatus for measuring the retroreflectivity of a reflective highway stripe or other retroreflective medium and which avoids the problems mentioned hereabove.

It is another object of this invention to provide a retroreflectivity measuring technique which simulates the retroreflectivity of the reflective medium as would be seen by a driver of a motor vehicle when the area is illuminated by the headlights of the vehicle.

It is yet another object of this invention to provide a method and apparatus for measuring retroreflectivity at normal, low viewing angles, but which can also be employed for testing retroreflectivity at high angles.

It is a still further object of this invention to provide a method and apparatus for measuring retroreflectivity at nearly any distance from several feet to several hundred feet by simply adjusting the elevation and/or aim of the component parts.

It is still another object of this invention to provide a method and apparatus for measuring retroreflectivity under ambient light conditions, including both day and night conditions, and regardless of the presence of rain, dust, etc.

It is a further object of this invention to provide a retroreflectivity measuring technique in which retroreflectivity can be measured at both high and low angles.

It is yet a further object of this invention to provide such a technique which can be carried out automatically.

According to several of many possible aspects of this invention, a method of measuring retroreflectivity of a reflective stripe or other reflective layer on a surface, involves illuminating a portion of the reflective layer with a laser beam of a predetermined wavelength, the laser beam being incident on the layer at a particular incidence angle i. The incident laser beam is then reflected back, and at least part of the reflected radiation is observed at a particular observation angle o that is separated by a divergence angle δ from the incidence angle i. The light that is reflected back at this observation angle o is filtered through a narrow pass optical filter whose pass band is centered on the predetermined wavelength of the laser beam, and the filtered reflected light is then picked up on a telephotomultiplier or other sensitive photometer. The photometer generates an electric level or other signal corresponding to the amount of light incident on it.

Because the laser produces a controlled, known amount of light, and the light is dispersed over a fixed, small area, the electrical signal produced by the photometer can be directly correlated to the reflectivity of the glass beads or other retroreflective particles in the layer. Preferably, the incidence angle i and the observation angle o represent the respective angular positions of vehicle's headlights and the eyes of the vehicle's driver. The divergence angle corresponds to the angular relationship between the eye position of the driver and the headlight position of the vehicle. The laser beam can be swept across the highway marker or stripe repeatedly and the retroreflectivity of the latter can thus be measured over its width. In addition, the sweeping motion of the beam has the advantage of maintaining a continuous signal in cases in which the stripe exhibits variations in direction.

Because the laser light is of a single frequency and is generated in a small controlled beam, the illuminated target area is illuminated by a known amount of light. Thus, the portion of that light returned to the observation point can be correlated to a fraction of the incident light. This solves one of the more serious problems of any low-angle optical system, that is, illuminating with a standard beam. Until now it has been impossible to control with any accuracy the area to be illuminated and measured for retroreflectivity.

In accordance with another of the many aspects of this invention, apparatus are provided for measuring the retroreflectivity of a reflective layer, comprising a laser-based optical illuminating device, operative for illuminating a portion of the reflective layer with a beam of a predetermined wavelength, and a telephotomultiplier for picking up the light reflected back at a particular observation angle, then filtering the light over a narrow pass band centered on the predetermined laser beam wavelength, and producing an electrical signal at a level corresponding to the intensity of the filtered reflected light, this level providing a measure of the retroreflectivity of the reflective layer. The laser device and the telephotomultiplier can be mounted together on a movable frame, for example, driven by a servo motor drive, for controlling the incidence angle and observation angle, and for scanning the retroreflective layer. In one preferred embodiment, the laser is a helium-neon laser having a wavelength of 632.8 nanometers or millimicrons, and the narrow pass band optical filter employed in the telephotomultiplier is an Oriel 5272 filter, which has a pass band of about 1 nanometer centered on the helium-neon laser light wavelength.

The above and many other objects, features, and advantages of this invention will be more fully understood from the ensuing description of certain preferred embodiments, which are given by way of example and not for purposes of limitation, as set forth in the ensuing detailed description which is to read in connection with the accompanying drawings, in which:

DESCRIPTION OF PREFERRED EMBODIMENTS

Figure 1:
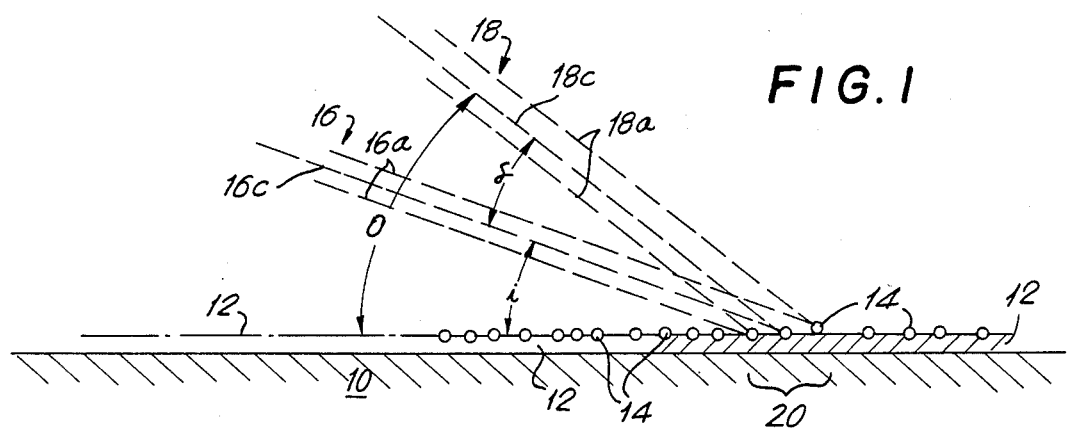
FIG. 1 is a schematic cross sectional view of a portion of a roadway surface, referred to for explaining the basic principles of this invention.

With reference initially to FIG. 1, the basic concept of the illustrated embodiments of this invention can be explained, in its simplest form, as an illumination of a target area with a laser beam at a desired incidence angle. As shown in FIG. 1, a roadway 10 has on its surface a painted marker stripe 12 on which there have been deposited a plurality of retroreflective spherical glass beads 14. Retroreflective particles, such as these glass beads 14, are particularly effective in adding retroreflectivity to roadway markings, so that nighttime visibility of the markings is greatly improved. For a number of reasons, the even distribution of these glass particles 14 over the painted surface of the stripe 12 is sometimes difficult to achieve. Also, because of weather and traffic conditions, the glass beads 14 can often be worn away or dislodged from the painted stripe 12, thus reducing the effectiveness of the retroreflective layer. This is particularly the case on roadway curves, bridge approaches, or the like, where the turning vehicle's tires impart a lateral shearing force against the painted stripe 12.

As is further shown in FIG. 1, an incident laser beam 16 impinges onto the stripe 12. The laser beam is of a uniform finite width, and is represented by a main or central ray 16c and side or edge rays 16a. The beam 16 impinges onto the roadway 10 at an incident angle i.

The laser light that impinges on the glass beads 14 is largely reflected in the direction generally back towards its source, so at least a portion of it would be reflected at a given observation angle o. This angle o is separated, as shown here, by a small separation angle delta from the incidence angle i. This reflected laser light at the observation angle o is illustrated here as a reflected beam 18 having a central ray 18c and edge rays 18a.

Typically, the laser beam as it emerges from a laser unit has an initial beam diameter of about 0.8 mm, but is expanded to a width of from about one to four inches in an optical beam expanding system. The latter is typically formed of a beam expander lens followed by a collimating lens. This lens system is generally known in the optical arts, so there is no need to illustrate it specifically here.

The laser beam 16 of finite width illuminates a target area 20. The size of the beam 16 is such that the area 20 that it illuminates is about one to four inches across, and thus the beam hits a large number of glass beads 14. However, the beam width is small enough that the spot or area 20 remains within the perimeters of the target stripe 12.

The intensity of the retroreflected laser beam 18 can be easily measured with a photometer. Because the intensity of the incident beam 16 is fixed and known, the measured intensity of the reflected laser light in the reflected beam 18 can be used directly for providing a measure of the retroreflectivity of the painted stripe 12.

Figure 2:
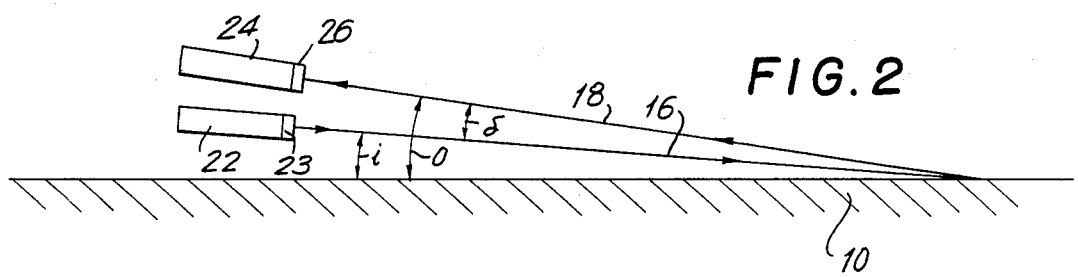
FIG. 2 is a simplified schematic view of the employment of the technique of this invention for measuring retroreflectivity at low angles.

In its basic form, as illustrated in FIG. 2, a laser 22, including a beam expanding lens system 23, and a telephotomultiplier 24 are mounted to illuminate the retroreflective particles 14 on the roadway 10 at a given low incidence angle i and to observe the reflected light 18 at a given low observation angle o. In this configuration, the incidence angle i and observation angle o, forming the divergence angle δ, can be selected to represent any given driver/headlight configuration at any distance. Here, the term low angle is used to mean angles of about 1° to about 5°, with respect to the horizontal. The laser 22 emits the incident laser beam 16 which impinges on the glass beads 14 and is reflected back as the beam 18, the latter being analyzed by the telephotomultiplier 24. A narrow band pass optical filter, having a narrow pass band (i.e., on the order of 1 nm) and centered on the wavelength of the laser beam 16, passes only that light being returned by the reflective beads 14 at the laser wavelength. The telephotomultiplier 24 can be moved to pick up the reflected light at any of various observation angles o, thus corresponding to various divergence angles δ.

This arrangement can be used to measure retroreflectivity at any distance from several feet to several hundred feet by adjusting the elevation and pitch of the laser 22 and the photometer 24. In addition, because of the sensitivity of the telephotomultiplier 24 and the narrow pass band of the filter 26, retroreflectivity can be measured under either night or day conditions, and regardless of the presence of rain.

Because the laser light is of a single wavelength and is generated in a small, controlled beam, the target area 20 illuminated by the laser beam 16 will receive a known amount of light. Thus, the portion of that light which is returned on the return beam 18 at the observation angle o can be measured, and this quantity can be used directly as a measure of the retroreflectivity of the surface in question.

Still further, the geometry of a measurement at any desired distance or angle can be simulated at a closer or longer distance simply by lowering or raising the laser 22 and telephotomultiplier 24 and changing their pitch. Satisfactory results can be obtained at slant distances, i.e., from the laser 22 to the target area 20, of less than about ten feet.

Figure 3:
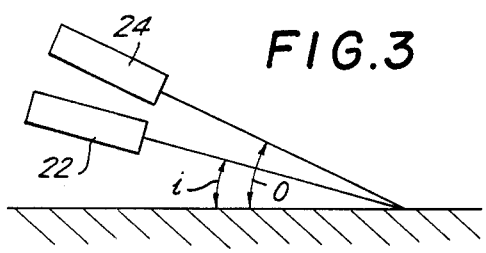
FIGS. 3 and 4 are simplified schematic views of alternate techniques for measuring retroreflectivity at relatively high angles.
Figure 4:
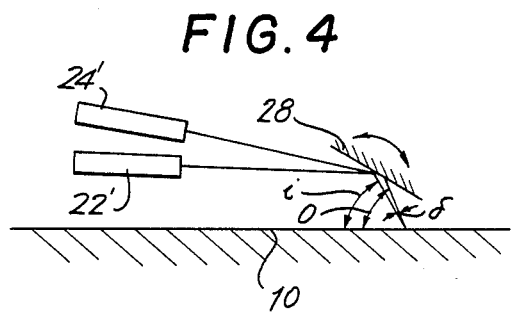

FIGS. 3 and 4 illustrate alternative techniques for obtaining retroreflectivity measurements at relatively high incidence angles (i.e., 15° to 60°). At these high angles, the differences in retroreflectivity attributable to bead embedment are minimized, and the resulting retroreflectivity reading is more directly related to the quantity of reflective beads 14 remaining in the painted stripe 12. The higher angle reflectivity measurements can be taken either by raising the laser 22 and telephotomultiplier 24, and then aiming them further downward, as shown in FIG. 3, or else by maintaining the pitch angles of the laser 22 and telephotomultiplier 24 constant, as shown in FIG. 4, while rotating one or more mirrors 28 for controllably changing the angles of incidence i and observation o from low to high. A single mirror 28 can be used for both the incident and reflected beams, or separate mirrors can be employed. In either possibility (FIG. 3 or 4) the laser-based retroreflectometer offers the capability of both high and low angle measurements in a single instrument.

A preferred laser instrument for use in this invention is a helium-neon laser, favorably of one or two milliwatts power.

Figure 5:
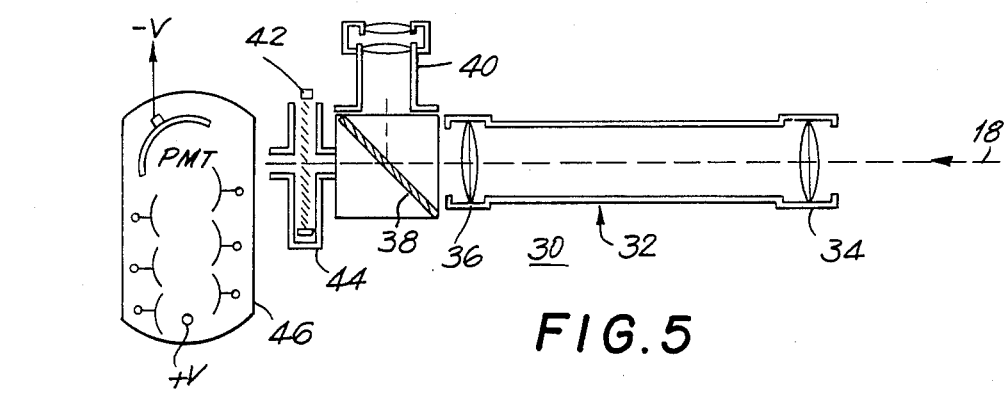
FIG. 5 is a schematic view of a telephotomultiplier which can be employed in connection with this invention.

A filtered telephotomultiplier 30 which can be employed with the techniques of this invention is shown schematically in FIG. 5. A telescope 32 of the photometer 30 is aligned with the observed retroreflected beam 18, and is focused on the spot or area 20 (FIG. 1) where the retroreflectivity is to measured. As is shown schematically in FIG. 5, the telescope 32 has an objective lens 34 and an ocular 36. A beam splitter 38 is disposed after the ocular 36 and sends part of the reflective beam 18 to an eyepiece 40, which can be used for visually aiming the telescope 32. The rest of the reflected beam 18 passes through the beam splitter 38, and thence through a filter 42 disposed in a filter holder 44, so that substantially only the narrow band of laser light passes therethrough to a multiplier phototube 46, shown schematically as following the filter 42. In a preferred embodiment, the filter 42 is an Oriel 5272 filter passing only a band of about 1 nanometer centered on the wavelength of the helium-neon laser. However, for other applications, other filters can be used. Also, for general use, either a neutral filter or a small pin hole can be employed, thus converting the telephotomultiplier 30 into a white light photometer.

While a multiplier phototube 46 of the type having a cathode and anode and a plurality of dynodes is shown schematically here, it should be recognized that many types of sensitive photoelectric cells could be equivalently employed.

Figure 6A:
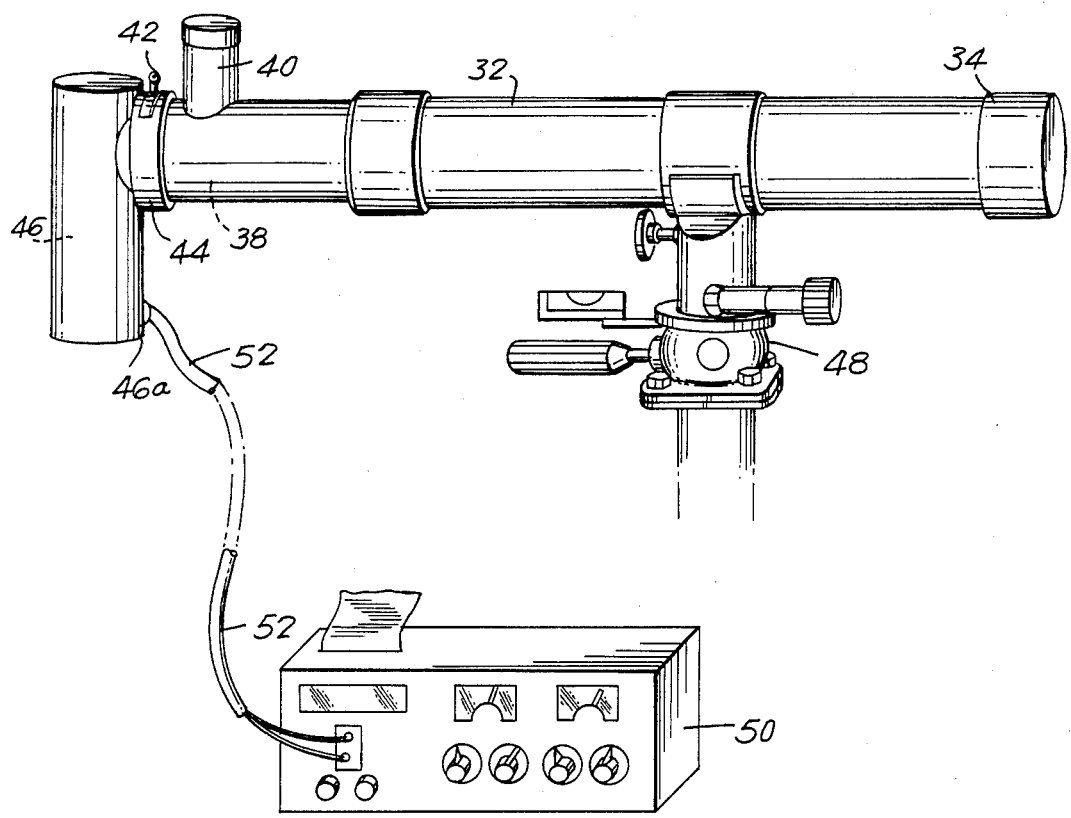
FIGS. 6A and 6B are perspective views of alternative arrangements of the telephotomultiplier employed in connection with this invention.

FIG. 6A is a perspective view illustrating a tripod-mounted telephotomultiplier which can be employed in connection with this invention. Here, the telescope 32 is mounted on a tripod 48. The multiplier phototube 46, here encased in a cylindrical housing 46a, is connected to a combined printing microvoltmeter and power supply 50 by means of a multi-conductor cable 52. A laser head (not shown) can be mounted on the tripod 48 at a position below the telescope 32. The other elements of FIG. 5 have corresponding reference numbers in FIG. 6, and a specific description thereof is omitted.

Figure 6B:
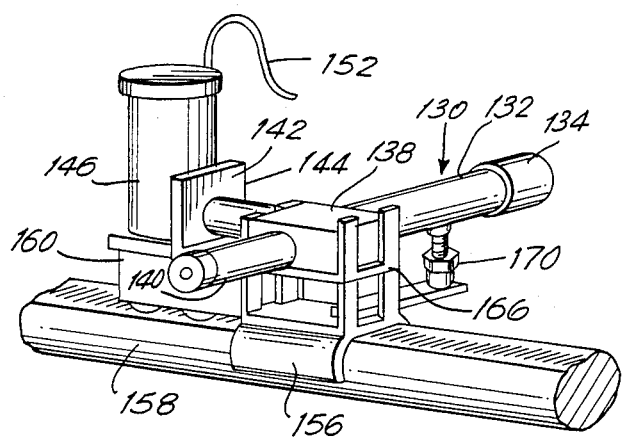

An alternative arrangement of the telephotomultiplier 130 of this invention is shown in Figure 6B. Here, the telephotomultiplier 130 has a telescope 132 with an objective lens 134 and a beam splitter 138, an eyepiece 140, a filter 142 mounted in a holder 144, and a multiplier phototube 146 having an associated cable 152. A frame 156 is movable along a rail 158 by means of a servo motor drive 160. The frame 156 supports a mount 166 for the telephotomultiplier 130 and an adjusting nut assembly 170 for adjusting the pitch of the telescope 132 to vary the observation angle o.

Figure 7:
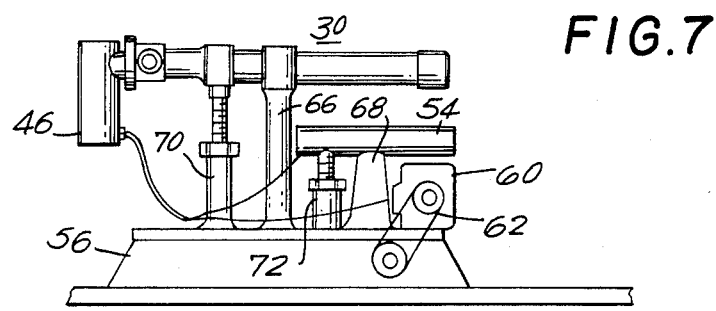
FIG. 7 illustrates manual apparatus according to this invention.

FIG. 7 illustrates one possible embodiment of an arrangement for automatic scanning of the painted marker stripe 12. In this embodiment a laser head 54, including not-shown beam expanding lenses, is mounted on a cart or frame 56, as is the telephotomultiplier 30. The cart or frame, in this embodiment, is movable laterally and is driven by a servo motor drive 60 having a chain drive 62 for driving the frame 56. A mount 66 pivotally supports the telephotomultiplier 30 and another mount 68 pivotally holds the laser head 54. Respective adjusting nut assemblies 70 and 72 are provided for adjusting the angles of observation and incidence by adjusting the pitch of the telephotomultiplier 30 and the laser head 54, respectively.

In this embodiment, the cable 52 includes conductors coupled to the laser head 54 and to the servo motor 60. The motorized frame 56 can thus be associated with a small computer or other data processing equipment, suitably programmed to cause the telephotomultiplier 30 and laser head 54 to scan along and/or back and forth across the target stripe 12. Data corresponding to the retroreflectivity of the stripe can be recorded, and the computer can be programmed to record the peak reading on each scan. In this configuration, the instrument can be mounted within a vehicle and moved along the road 10 to obtain a large sample of readings, which would be more representative of the retroreflectivity of the painted stripe 12 than would be a single reading or only several readings. Also, because of the mobility of the arrangement of FIG. 7, readings can be obtained relating to performance and bead retention at specific locations, such as curves in the roadway 10.

With this arrangement, the scan of the laser head 54 and the telephotomultiplier 30 can be aimed digitally and can be kept aimed at the stripe 12 by the computer program. That is, the scan boundaries can be digitally controlled, and compared, e.g., with low reflectivity measurements characteristic of the boundaries, so that the laser head 54 and telephotomultiplier 30 are kept aimed towards the center of the stripe 12. Where there is a double line present, such as in the case of a no-passing zone double centerline, the aiming of the telephotomultiplier 30 and the laser 54 can be digitally controlled so as to read and record the proper retroreflectivity measurement for each line, in either a high or low angle position, or in both positions.

In the embodiments of FIG. 7, the adjusting assembly 70 can be automatically driven, using a separate servo motor control (not shown) or can be manually adjusted.

Figure 8:
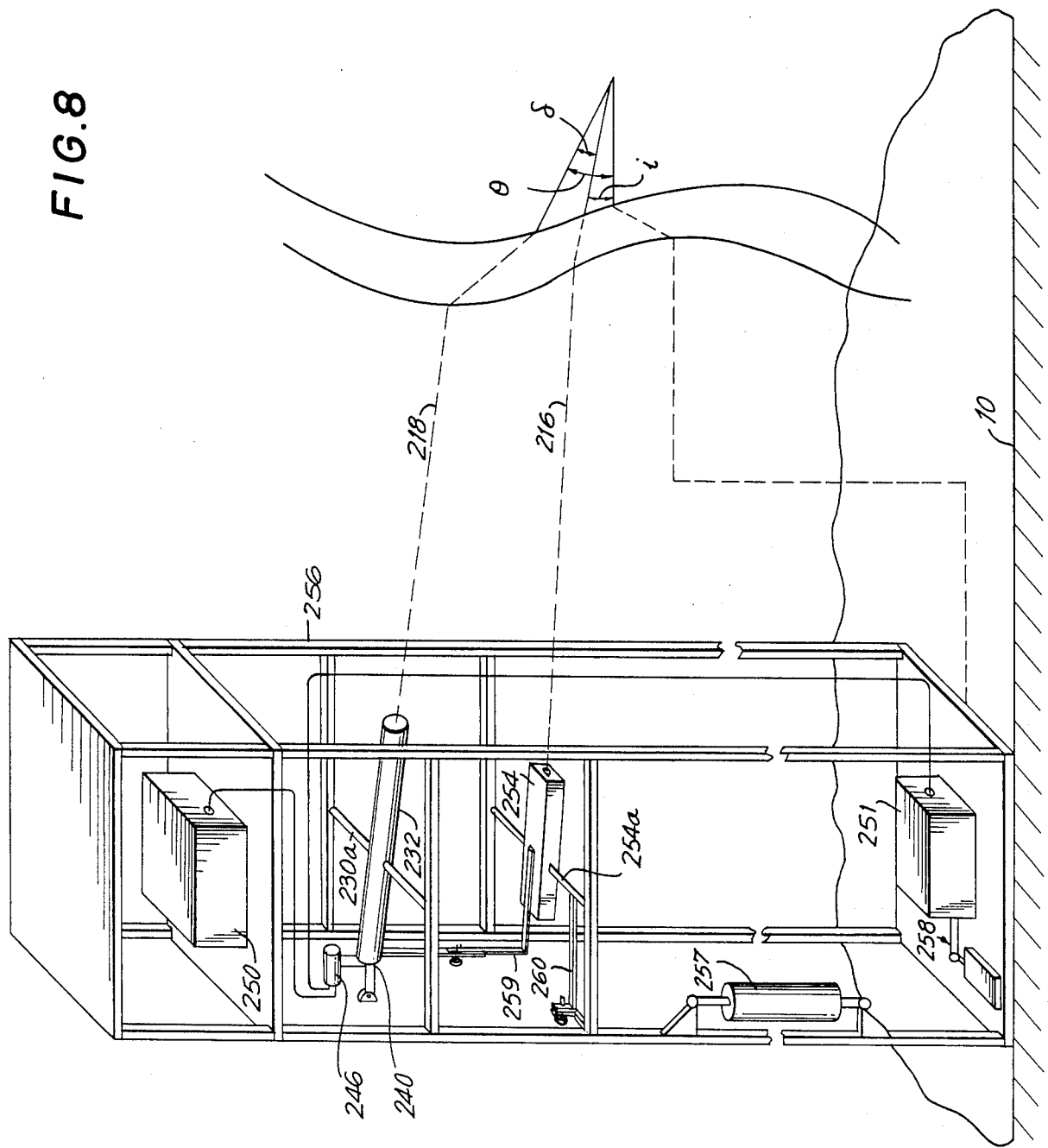
FIG. 8 illustrates schematically an automatic arrangement of a laser reflectometer of this invention.

An automated laser retroreflectometer is illustrated schematically in FIG. 8. In this embodiment, a telephotomultiplier having a telescope 232, an eyepiece 240 and a multiplier phototube 246 is pivotally mounted in a horizontal shaft 230a carried by a frame 256. A laser head 254 is pivotally mounted below the telephotomultiplier 230 by a horizontal axis 254a onto the frame 256. A microprocessor-based controller and microvoltmeter 250 is mounted on an upper part of the frame 256, and a power supply for the laser 254 is mounted on the lower part of the frame 256. The frame 256 rests on the roadway surface 10, and includes an elevating mechanism 257 for raising or lowering the upper part of the frame 256 and a rotating mechanism 258 for rotating the frame 256 in a sweeping fashion.

An adjustable linkage 259 joins the telephotomultiplier and the laser 254 so that they pivot together on their respective shafts 230a and 254a. Another linkage 260 controls the pitch angle of the laser 254 relative to the frame 256.

With this arrangement, the pitch of the laser 254 and the telephotomultiplier, their height and their azimuth can be controlled and changed automatically from the microprocessor controller 250, directing these elements along the appropriate angles of incidence i and observation o.

Figure 9:
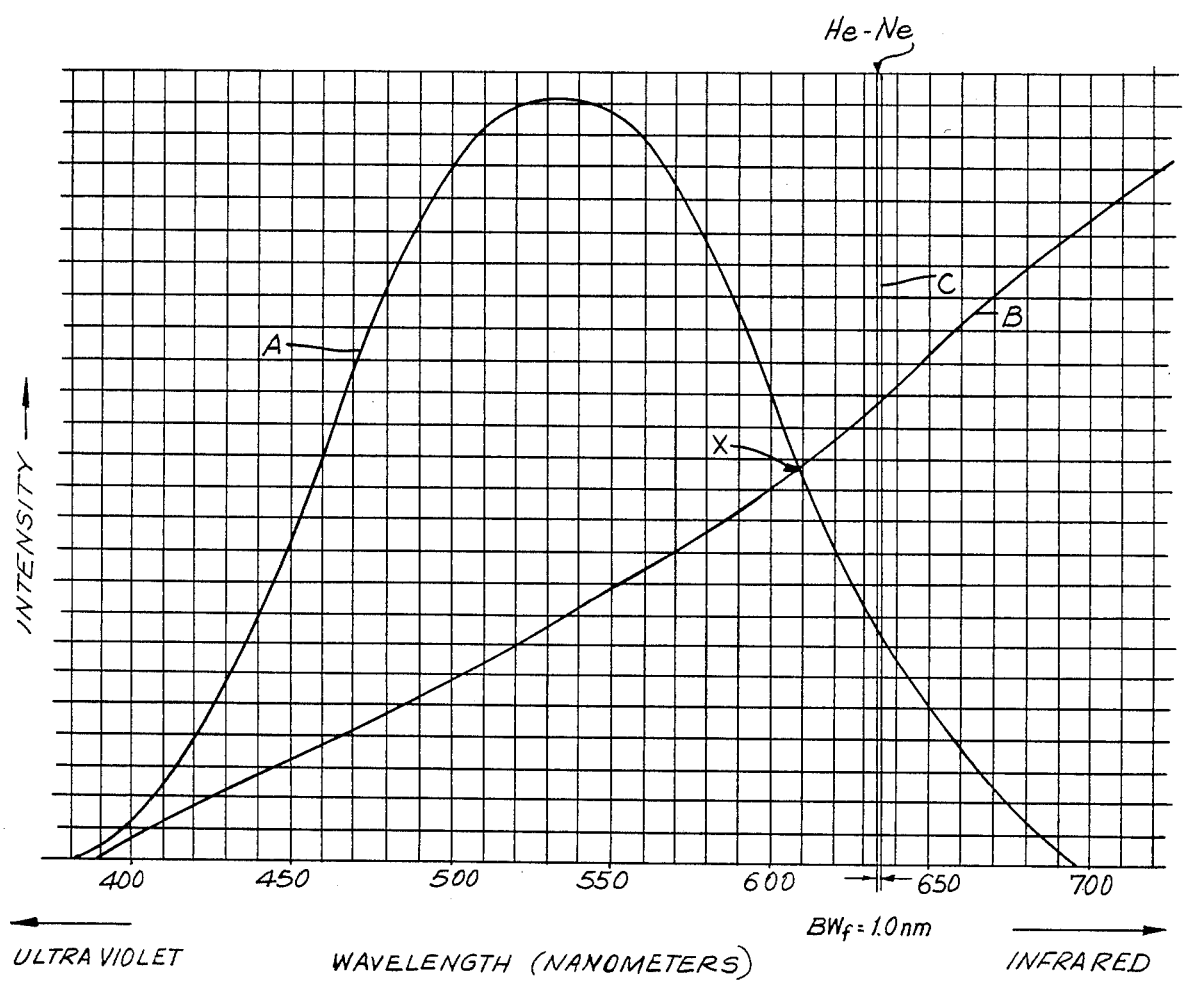
FIG. 9 is a chart of intensity versus wavelength for explaining the operation and advantages of this invention.

The optical characteristics of the preferred helium-neon laser, and the associated filter 42 or 142 are illustrated in the chart of FIG. 9. Here, curve A represents the approximate sensitivity of the human eye to visible light, and curve B represents the approximate frequency distribution of a tungsten incandescent lamp, such as an automotive headlamp. The sensitivity of the human eye to the light of the headlamp will be greatest near the crossing point X of the curves A and B, that is, for wavelengths of about 600–650 nm. Accordingly, wavelengths in this range are representative of optimal night vision conditions. Curve C, which is a single vertical line, represents the wavelength distribution of the helium-neon laser as used in the preferred embodiment of this invention. This laser emits light at the single wavelength of 632.8 nm. As shown on the abscissa of FIG. 9, the Oriel 5272 filter 42 used in the telephotomultiplier has a filter bandwidth $BW_f$ of only about 1.0 nanometers, centered on the helium-neon laser wavelength 632.8 nanometers.

Because the laser head 54 generates light at a specific wavelength and the filter 42 passes light of only that wavelength, reflectivity measurements can be taken with the arrangements of this invention during either day or night conditions, or in the presence of artificial lights, without affecting the readings significantly. Also, the instrumentation of this invention provides reliable readings on either rainy or dry conditions during light fogs, or under other conditions where other techniques, not employing a laser and an associated filter, would be impractical.

Of course, lasers other than helium neon lasers can be used acceptably, provided that they reasonably represent night time vision.

Figure 10:
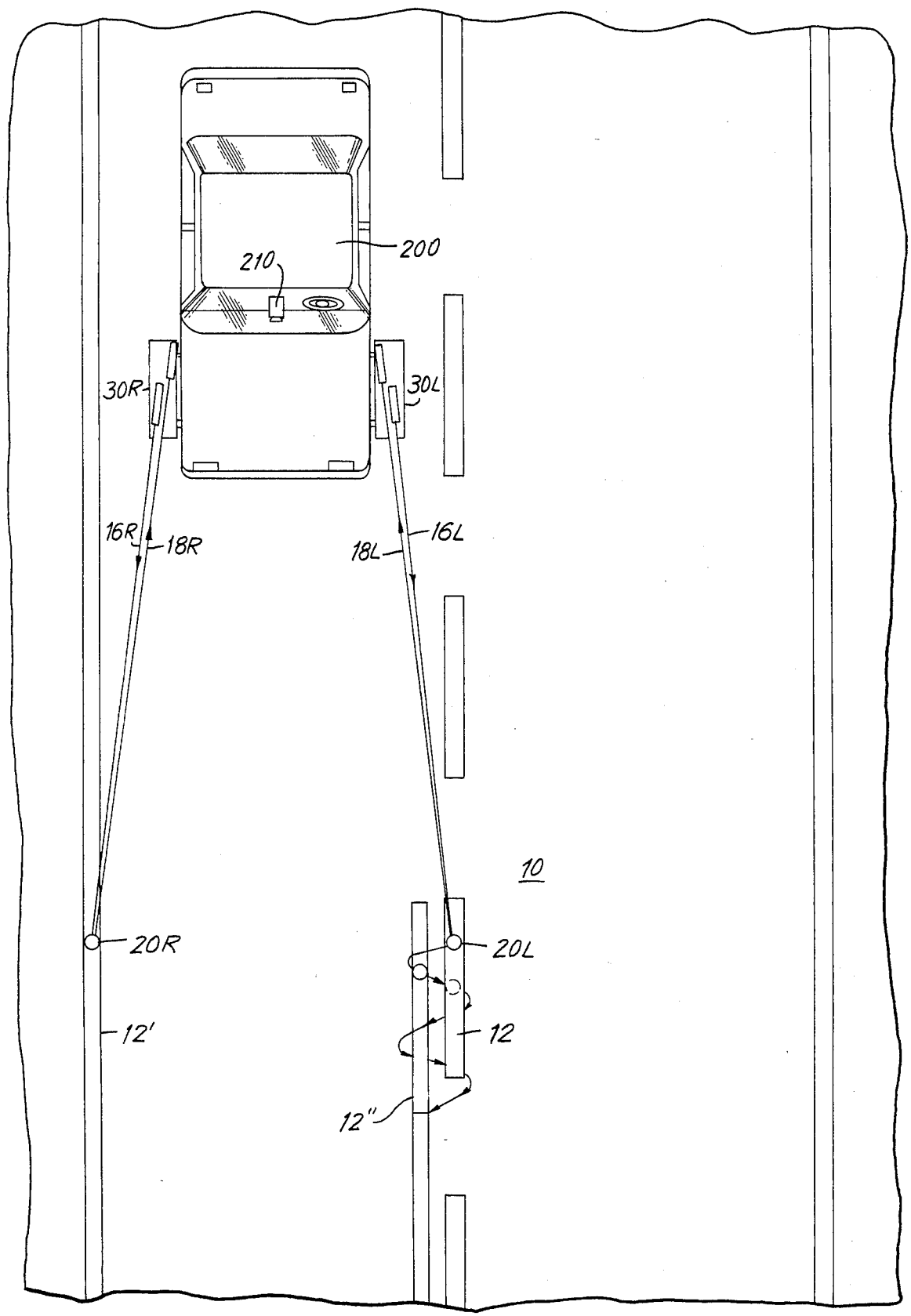
FIG. 10 is an environmental view showing a practical arrangement of this invention.

FIG. 10 illustrates a specific practical arrangement of this invention employed for measuring the performance of reflective beads on a roadway surface 10. Here, a vehicle 200 is provided with retroreflectometers 30L and 30R mounted on the left and right sides thereof. Each retroreflectometer 30L, 30R emits a respective laser beam 16L and 16R, which impinges on a stripe, such as the broken roadway center line 12 or the outer lane marker stripe 12'. The laser beam 16L forms a spot 20L which can be scanned back and forth as the vehicle 200 is moving. Here, the beam 16L forms the spot 20L and scans it back and forth across the stripe 12 and also across a no-passing solid line 12''. A small onboard computer within the vehicle 200 can record numerical data relating to the retroreflectivity of the stripes 12, 12' and 12''. A video camera 210 is mounted near the driver position in the vehicle 200 so that the driver's view and numerical performance data can be recorded simultaneously.

The technique including the method and the apparatus of this invention improves highway safety by providing accurate, quick, and reliable testing of the reflective nature of the highway stripes and other markings, and can provide bead retention data at selected locations, so that appropriate roadway maintenance can be facilitated.

While several embodiments of this invention have been shown and particularly described hereinabove, it should be recognized that many modifications and variations thereof would present themselves to those persons of ordinary skill in the art without departing from the scope and spirit of this invention, as defined in the appended claims.

What is claimed is:

1. A method of measuring retroreflectivity of a reflective layer on a surface, comprising:

illuminating a portion of said reflective layer with a laser beam of a predetermined wavelength emanating from a laser source while said portion is exposed to ambient light, said wavelength being in the range of from about 600 nm to about 650 nm and said laser beam being incident on said layer at a particular incidence angle (i), said incident beam being reflected in the direction generally back toward its source at least partially at a particular observation angle (o), said incidence angle and said observation angle being separated by a divergence angle ($\delta$);

filtering the laser light reflected at said observation angle through a narrow pass filter centered on said predetermined wavelength;

picking up said filtered light with a photometer; and producing an electric signal corresponding to the amount of light incident on said photometer, said signal thus corresponding to the retroreflectivity of the illuminated portion of said reflective layer.

2. A method of measuring retroreflectivity according to claim 1, wherein said incidence angle (i) is less than said observation angle (o), such that said divergence angle ($\delta$) corresponds to the angular relationship between the eye position of a driver of a vehicle and the headlight position thereof.

3. A method of measuring retroreflectivity according to claim 1, wherein said incidence angle and said observation angle are on the order of about one to five degrees.

4. A method of measuring retroreflectivity according to claim 1, wherein said incidence angle and said observation angle are between about 15° and 60°.

5. A method of measuring retroreflectivity of a reflective stripe on a road surface, said strip containing beads of a generally transparent material, comprising:

sweeping a laser beam across said stripe at a particular incidence angle relative to said stripe to illuminate an area of said stripe while the stripe is exposed to ambient light, said incident laser beam being reflected back at least partially at a particular observation angle;

sweeping a telephotomultiplier across said stripe at said observation angle to trace the sweeping of the incident beam, said telephotomultiplier producing an output level related to the amount of said incident laser beam that is reflected back at said observation angle; and ascertaining said retroreflectivity based on the output level of said telephotomultiplier.

6. A method of measuring retroreflectivity of a reflective marking on a road surface, said marking containing reflective beads of a generally transparent material comprising:

sweeping a laser beam emanating from a laser source across said marking at a particular incidence angle relative to said marking to illuminate an area of said marking while said area is exposed to ambient light, said incident beam having a predetermined wavelength in the visible spectrum and being reflected in the direction generally back toward its source at least partially at a particular observation angle;

sweeping a telephotomultiplier across said marking at said observation angle to trace the sweeping of the incident beam, said reflected beam being filtered in said telephotomultiplier through a narrow pass filter centered on said predetermined wavelength and then incident on a photometer element, said photometer element producing an output level related to the amount of said incident laser beam that is reflected back at said observation angle; and ascertaining the retroreflectivity of said marking based on the output level of said telephotomultiplier.

7. A method of measuring retroreflectivity of a reflective light on a surface, comprising:

illuminating a portion of said reflective layer with a laser beam of a predetermined wavelength emanating from a laser source while said portion is exposed to ambient light, said wavelength being in the range of from about 600 nm to about 650 nm and said laser beam being directed to incidence mirror means and being reflected thereby to be incident on an area of said layer at an incidence angle, said incident beam being reflected in the direction generally back toward its source at least partially at an observation angle;

reflecting the light reflected back at said observation angle in observation mirror means;

filtering the light reflected back from said observation mirror means through a narrow pass filter centered on said predetermined wavelength; and picking up the filtered light with a photometer corresponding to the amount of light incident on said photometer, said level thus corresponding to the retroreflectivity of the illuminated portion of said reflective layer.

8. A method of measuring retroreflectivity according to claim 7, further comprising controllably rotating each of said mirror means to change said incidence angle and said observation angle.

9. A method of measuring retroreflectivity according to claim 7, wherein said incidence angle and said observation angle are between about 15° and 60°.

10. A method of measuring retroreflectivity of a reflective layer on a surface, comprising:

illuminating a portion of said reflective layer with a laser beam emanating from a laser source while said portion is exposed to ambient light, said beam being of a predetermined wavelength, said laser beam being incident on said layer at a low incidence angle, said low incidence angle being on the order of about 1° to 5° from horizontal, said beam being reflected in the direction generally back toward its source, at least partially at a similarly low observation angle, said incidence angle and said observation angle being different from each other and separated by a divergence angle;

measuring with a photometer the intensity of the laser light reflected back at said low observation angle;

illuminating said portion of said reflective layer with said laser beam incident thereon at a high incidence angle, said high incidence angle being on the order of 15° to 60° from the horizontal, said beam being reflected in the direction generally back toward its source, at least partially, at a similarly high observation angle, said high incidence and observation angles being separated by a divergence angle;

measuring with said photometer the intensity of the light reflected back at said high observation angle; and averaging the measured intensities of said reflected back light at said high and said low observation angles, thus producing an indication of the condition of the reflective layer.

11. A method according to claim 10, wherein said laser and said reflectometer are raised and lowered to change to and from said high and low angles of incidence and observation.

12. Apparatus for measuring the retroreflectivity of a reflective layer on a surface, comprising:

laser illumination means for illuminating a portion of said reflective layer with a laser beam of a predetermined wavelength while said portion is exposed to ambient light, said wavelength being in the range of from about 600 nm to about 650 nm and said laser beam being incident on said layer at a particular incidence angle and being reflected in a direction generally back toward the laser illumination means at least partially at a particular observation angle;

telephotomultiplier means for picking up the light reflected back at said observation angle, filtered the light over a narrow pass band centered on said predetermined wavelength, and producing an electrical level corresponding to the intensity of the filtered reflected light, and thus providing a measure of the retroreflectivity of said reflective light, and thus providing a measure of the retroreflectivity of said reflective layer; and means mounting said laser means and said telephotomultiplier means for aiming said laser means and said telephotomultiplier means for illuminating said layer at said incidence angle and receiving the light retroreflected therefrom at said observation angle.

13. Apparatus for measuring the retroreflectivity of a reflective highway marking layer on a surface, comprising laser illumination means for illuminating a portion of said reflective layer with a laser beam of a predetermined wavelength while said portion is exposed to ambient light, including means for expanding said laser beam to a beam width on the order of several inches, said expanded laser beam being incident on said layer at a particular incidence angle and being reflected back at least partially at a particular observation angle;

telephotomultiplier means for picking up the light reflected back at said observation angle, filtering the light over a narrow pass band centered on said predetermined wavelength, and producing an electrical level corresponding to the intensity of the filtered reflected light, and thus providing a measure of the retroreflectivity of said reflective layer; and means mounting said laser illumination means and said telephotomultiplier means for illuminating said layer at said incidence angle and receiving the light retroreflected therefrom at said observation angle.

14. Apparatus for measuring the retroreflectivity of a reflective highway marking layer on a surface, comprising:

laser illumination means for illuminating a portion of said reflective layer with a laser beam of a predetermined wavelength while said portion is exposed to amblient light, said wavelength being in the range of from about 600 nm to about 650 nm and said laser beam being incident on said layer at a particular selected incidence angle and being reflected in the direction generally back toward the laser illumination means at least partially at a particular observation angle;

telephotomultiplier means for picking up the light reflected back at said observation angle, and having an objective end and an ocular end, a beam splitter at the ocular end of said telescope for splitting the beam emerging from said ocular end into first and second beams, an eyepiece disposed at said beam splitter for viewing said first beam, filter means disposed along said second beam for passing only light within a narrow band centered on the predetermined wavelength of said laser beam, and photometer means disposed after said filter means for producing an electric level in relation to the intensity of the filtered second beam incident thereon; and means mounting said laser means and said telephotomultiplier means for illuminating said layer at said incidence angle and receiving the light retroreflected therefrom at said observation angle.

15. Apparatus according to claim 14, wherein said filter means includes a filter having a pass bandwidth of substantially one nanometer.

16. Apparatus according to claim 14, wherein said filter means includes a filter holder and a filter removably disposed therein.

17. Apparatus for measuring the retroreflectivity of a reflective highway marking layer on a surface, comprising:

laser illumination means for illuminating a portion of said reflective layer with a laser beam of a predetermined wavelength while said portion is exposed to ambient light, said wavelength being in the range of from about 600 nm to about 650 nm and said laser beam being incident on said layer at a particular incidence angle and being reflected back at least partially at a particular observation angle;

telephotomultiplier means for picking up the light reflected back at said observation angle, filtering the light over a narrow optical pass band centered on said predetermined wavelength, and producing an electric level corresponding to the intensity of the filtered reflected light, thus providing a measure of the retroreflectivity of said reflective layer; and means mounting said laser illumination means and said telephotomultiplier means for illuminating said layer at said incidence angle and receiving the light retroreflected therefrom at said observation angle, the mounting means including a frame and controlled motor drive means on said frame for scanning said laser illumination means and said telephotomultiplier means across said reflective layer.

18. Apparatus according to claim 17, wherein said controlled motor drive means includes means for repeatedly sweeping said laser beam and said telephotomultiplier means across said reflective layer.

* * * * *